US008751249B2

(12) United States Patent
Palmer et al.

(10) Patent No.: US 8,751,249 B2
(45) Date of Patent: Jun. 10, 2014

(54) SYSTEM AND METHOD FOR CAPTURE OF QUALIFIED COMPLIANCE DATA AT POINT OF CLINICAL CARE

(75) Inventors: Patricia A. Palmer, Kansas City, MO (US); Karen S. Berg, Mission, KS (US)

(73) Assignee: Cerner Innovation, Inc., Kansas City, KS (US)

(*) Notice: Subject to any disclaimer, the term of this patent is extended or adjusted under 35 U.S.C. 154(b) by 2345 days.

(21) Appl. No.: 11/025,998

(22) Filed: Jan. 3, 2005

(65) Prior Publication Data

US 2006/0149590 A1 Jul. 6, 2006

(51) Int. Cl.
*G06Q 10/00* (2012.01)
*G06Q 50/00* (2012.01)
*A61B 5/00* (2006.01)
*G06F 19/00* (2011.01)

(52) U.S. Cl.
USPC .................................................. 705/2; 705/3

(58) Field of Classification Search
USPC .......................................... 705/2–3; 600/300
See application file for complete search history.

(56) References Cited

U.S. PATENT DOCUMENTS

| | | | | |
|---|---|---|---|---|
| 6,108,635 | A * | 8/2000 | Herren et al. ...................... | 705/2 |
| 6,529,876 | B1 * | 3/2003 | Dart et al. ........................... | 705/4 |
| 7,734,481 | B1 * | 6/2010 | Hutton et al. ....................... | 705/3 |
| 2003/0083903 | A1 * | 5/2003 | Myers ................................. | 705/2 |
| 2003/0115083 | A1 * | 6/2003 | Masarie et al. .................... | 705/2 |
| 2003/0120516 | A1 * | 6/2003 | Perednia ............................ | 705/3 |

OTHER PUBLICATIONS

Karen Sandrick, Everything You Want to Know About the Joint Commission, Jun. 2004, Trustee, 57, 6, pp. 17-20.*

* cited by examiner

*Primary Examiner* — Joy Chng
(74) *Attorney, Agent, or Firm* — Shook, Hardy & Bacon LLP (57) ABSTRACT

A system and related techniques generate and maintain a set of compliance-qualified data schemas or templates for deployment in a hospital or other clinical setting. According to conventional implementations, the clinical data required by regulatory reporting bodies such as CMS (Centers for Medicare and Medicaid Services), JCAHO (Joint Commission on Accreditation of Healthcare Organizations) or other government or private bodies may not be systematically captured or track, so that compliance officers and other managers are left to reconstruct compliance data after the face, for instance from patient accounting systems or other platforms not designed to filter or store regulatory data. Platforms and methods according to the invention, in contrast, may access regulatory or compliance criteria and generate a data capture or documented care template, according to which various clinical measures and other information which are required by compliance bodies are automatically captured, at the point of care. Thus patient labs, tests, outcomes and other clinically related data may be conditioned to include that information demanded by regulatory standards, including lab ratios and others, and that data may be automatically recorded, stored, and in embodiments, transmitted to regulatory bodies or agencies, electronically. The regulatory data store that results may likewise in embodiments be accessed by analytic tools to model various compliance and clinical scenarios.

34 Claims, 4 Drawing Sheets

SYSTEM AND METHOD FOR CAPTURE OF QUALIFIED COMPLIANCE DATA AT POINT OF CLINICAL CARE

CROSS-REFERENCE TO RELATED APPLICATION

The subject matter of this application is related to the subject matter of U.S. Provisional patent application Ser. No. 10/720,086 filed Nov. 25, 2003 entitled "System and Method for Evidence-Based Modeling of Operations", which application is owned or under obligation of assignment to the same entity as this application, and which application is incorporated by reference herein.

STATEMENT REGARDING FEDERALLY SPONSORED RESEARCH OR DEVELOPMENT

Not applicable.

FIELD OF THE INVENTION

The invention relates to the field of clinical information technology, and more particularly to systems and methods for capturing an array of clinical data at the point of medical care delivery, which data is qualified to satisfy regulatory or compliance requirements and which may be automatically communicated to regulatory or governing bodies.

BACKGROUND OF THE INVENTION

The steady expansion and diversification of the health-care industry has led in many regards to a corresponding expansion in the depth, detail and sophistication of regulatory and other reporting requirements which health-care providers face. Hospitals, research institutions and other clinical or medical facilities must consider and satisfy an array of government and industry reporting criteria, including those imposed or applied by the Centers for Medicare and Medicaid Services (CMS), the Joint Commission on Accreditation of Healthcare Organizations (JCAHO), and other public, private, federal, state and other agencies or bodies. Those regulatory or reporting criteria may be required for a variety of purposes, including for purposes of public or private bill payment or reimbursement, professional or clinical accreditation, disease surveillance, census and other purposes. Many of those criteria may be legally mandated, for instance to ensure adherence to best practices and other purposes, and those mandates may change over time. In other cases, the amount or percentage of medical bills which CMS or other payors may agree to pay may depend upon the overall clinical outcomes and documented care delivered by a hospital or other institution.

However, compliance officers and others with regulatory reporting responsibilities may discover that their institutions lack appropriate tools to timely and thoroughly meet the complex regulatory requirements they are charged with satisfying. For example, CMS and other criteria may require that patients with certain classes of diseases or conditions have various blood test, imaging, electrocardiograph and other clinical or medical documentation to have the costs for their medical services reimbursed or paid by Medicare or other plans.

However, many hospitals and other clinical sites lack a ready way to produce that type of clinical data backup for all but the most rudimentary or incomplete data. In many cases, the hospital may rely on the internal patient accounting system, which may be built for billing purposes rather than to track the diverse, rich set of clinical information necessary for all phases of compliance. Thus when a CMS, JCAHO or other requirement calls for documentation that a patient's pneumonia or other diagnosis and treatment was supported by blood gas readings within a certain range, or the ratio of blood readings to other data such as patient population, age brackets or others, the account records may not, and typically do not, contain the clinical data to a sufficient level of detail to meet the requirement.

Moreover, by the time that regulatory compliance is performed, in many settings it may be one or two months or more after the clinical encounter occurred. Retrospectively examining patient accounting records in a period of time after the patient care was delivered often results in no useable data for compliance purposes, at all. Therefore compliance personnel may be forced to have patient charts and other electronic or paper records examined manually, to determine adherence to the regulatory criteria. Besides being time-consuming and prone to human error, certain pieces of data which are called for by the regulatory or other standards body may not exist in any form, after some amount of time after care. Or, that data may not have been captured at any point in the patient's treatment, since patient accounting and other systems used for the ad hoc purpose of acting as a compliance data store may not require, include or condition inputs on compliance requirements. In those and other cases reporting compliance, or the accuracy or completeness of that reporting, can not be ensured. These and other problems in clinical data capture and reporting systems exist.

SUMMARY OF THE INVENTION

The invention overcoming these and other problems in the art relates in one regard to a system and method for the capture of qualified compliance data at a point of clinical care, in which compliance-qualified data may be captured at a point of clinical care or medical service, for instance using a documented care template or format which encodes compliance information and measures necessary to meet reporting requirements. According to embodiments in one regard, a conditioning engine may access government, private or other compliance criteria and generate a documented care template which may be used to capture contemporaneous or near-contemporaneous clinical data such as laboratory test results, imaging studies, pharmaceutical prescription or use, clinical outcomes or other data. That data may be captured and stored into a documented care note, chart or other record, which may in embodiments be stored to a clinical data store. According to embodiments in a further regard, the documented care record may be automatically transmitted to a compliance or regulatory body, such as the Centers for Medicare and Medicaid Services, JCAHO, or various other federal, state, local, public or private bodies or organizations, for instance at scheduled times, episodically or at other times. Because among other things, the documented care record may contain much, most or all of the clinical information necessary to satisfy compliance standards, clinical managers and others may be relieved of the task of retrospectively backtracking through inaccurate or incomplete records to supply compliance verification. Rather, the reporting information is captured as a byproduct of documentation of the care delivered in the healthcare setting. The documented care record may in one regard generate or contain core clinical measures including test ratios such as those related to blood-test results, synthesized and aggregated into data that describes the findings across defined patient populations and others, automatically satisfying even more extensive compliance requirements in one integrated process.

DETAILED DESCRIPTION OF EMBODIMENTS

Figure 1:
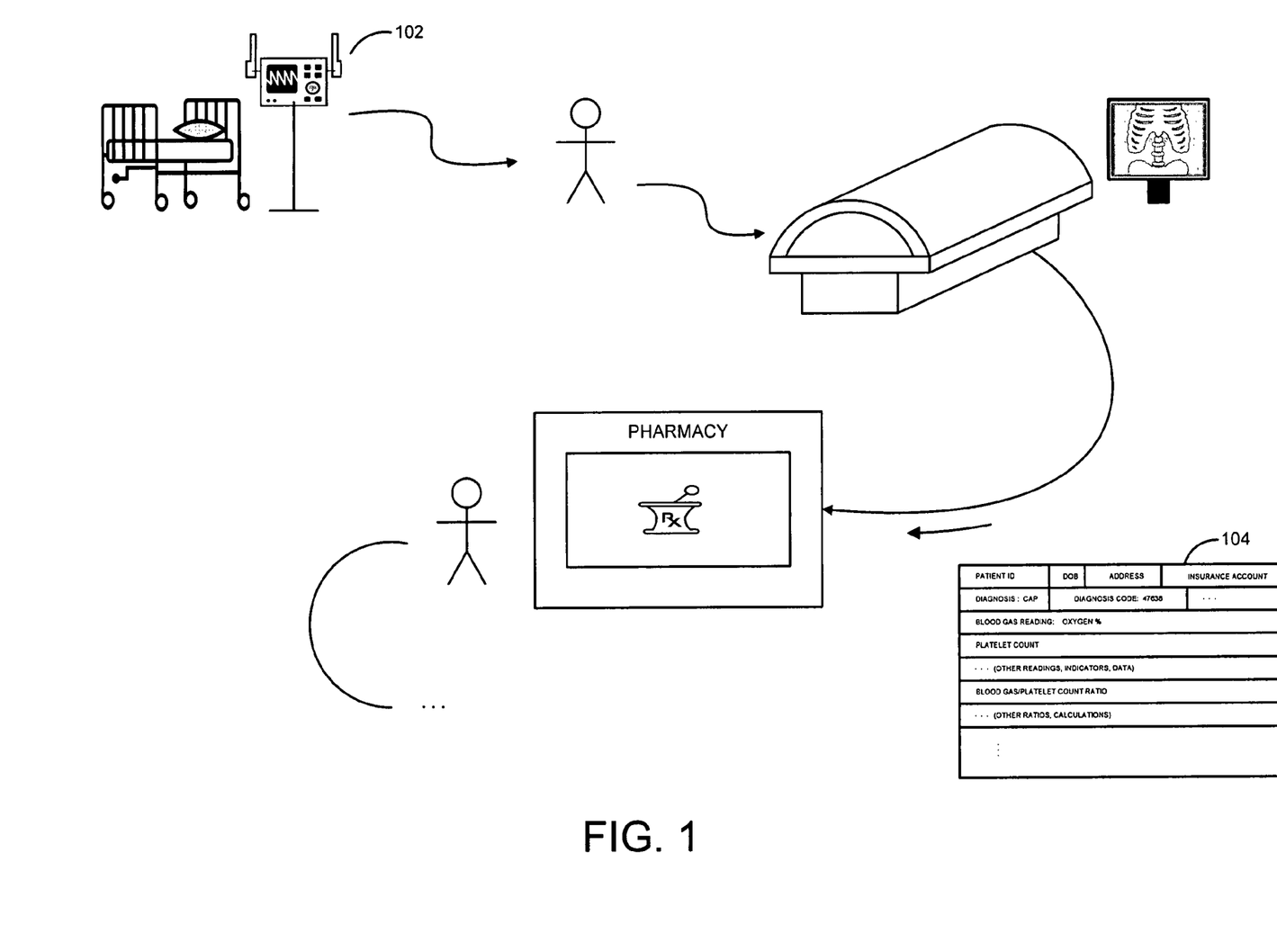
FIG. 1 illustrates an example of a progression of clinical encounters and medical services delivered through one or more point of care, according to embodiments of the invention.

FIG. 1 illustrates an environment in which a system and method for the capture of qualified compliance data may operate, according to embodiments of the invention.

As illustrated in that figure, a patient or other recipient of medical or clinical care may receive or accept medical care or attention at a point of care 102 or series of such points of care. Point of care 102 may be or include, for instance, a hospital including a hospital emergency room, an operating room, a hospital bed, an X-ray, MRI (magnetic resonance imaging), CAT (computerized axial tomography) scan or other imaging room, equipment or station, an urgent care facility, a rehabilitative care facility, a mobile care facility such as an ambulance, helicopter or EMT vehicle, a robotic or other remote surgical, diagnostic reading or other site or facility, a pharmacy or other site or store for pharmaceuticals or drugs, or other site, facility, or location. The patient or other care recipient may proceed through one or more point of care 102 receiving clinical treatment, diagnostic testing or other care for the same, related or unrelated illnesses or conditions, within the course of one encounter, over the course of hours, days, weeks or other period of hospitalization, or at other different or unrelated times.

Figure 2:
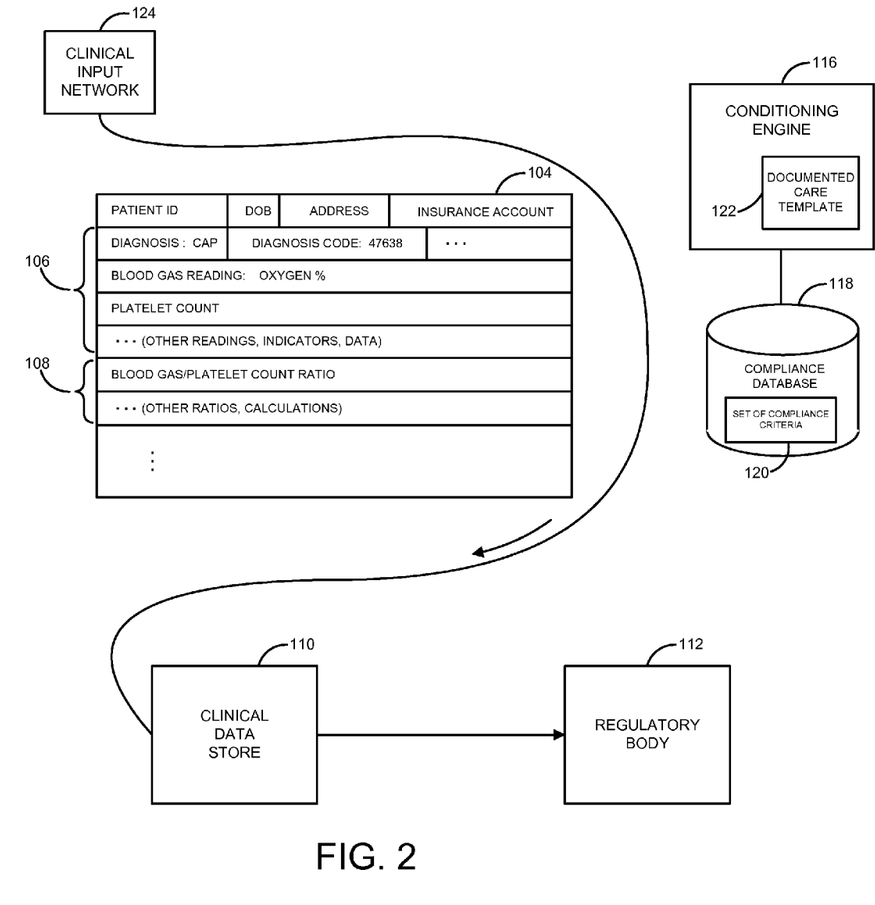
FIG. 2 illustrates a documented care record and associated information, according to embodiments of the invention.

According to embodiments of the invention in one regard, and as for example illustrated in FIG. 2, as the patient or other care recipient proceeds in one or more clinical encounter at one or more point of care 102, clinical data generated by or related to the care delivered at the point of care 102 may be detected and captured. More particularly, at or in proximity to point of care 102, and contemporaneously, near-contemporaneously or at other times relative to the clinical care encounter, clinical or clinically-related data may be captured via a clinical input network 124. For instance, electrocardiogram (EKG), electroencephalogram (EEG) or other electrical study or data, an X-ray, MRI, CAT or other imaging study or data, blood-derived laboratory tests such as blood oxygen levels, platelet counts, antibody tests, protein levels, toxicity studies, patient history, blood pressure or other clinical, medical, dental or other data or information may be received via clinical input network 124. Clinical input network 124 may be, include or interface to various information input channels or records including, for instance, direct electronic instrument readings, automatically logged or manually inputted laboratory test results, electronic medical records, or other clinical annotations, documents or information.

According to embodiments of the invention in one regard, the type and nature of the clinical care data captured at point of care 102 may be qualified by, conditioned on or adapted to a set of compliance criteria 120, for purposes of regulatory reporting and other compliance activity. More specifically, according to embodiments of the invention in one regard, a conditioning engine 122 may access the set of compliance criteria 120, for instance in a compliance database 118, to identify and capture the set of clinical data, metrics, measures and other information required for the reporting requirements of the hospital or other clinical site or organization to a documented care record 104. The set of compliance criteria 120 may be used by conditioning engine 116 to generate a documented care template 122 or other structured data object which requires data, fields, computations, procedures or other inputs necessary to support compliance activity. An example of a generalized documented care template is for example described in U.S. Pat. No. 5,715,449 entitled "Method for Generating Structured Medical Text Through User Selection of Displayed Text and Rules", which is incorporated by reference herein. Compliance criteria 120 may illustratively be or include, for example, criteria such as those promulgated by JCAHO related to the diagnosis and treatment of patients experiencing an acute myocardial infarction (AMI), including the administration of an aspirin regimen and other care, as specified in "Specifications Manual for National Implementation of Hospital Core Measures", Version 2.0, Measure Information Forms (MIFS), Section AMI-1, or other sections of or criteria in that manual applicable to other diagnoses or events, and which manual is incorporated in entirety by reference herein. Other types, kinds and sources of the set of compliance criteria 120 are possible. In embodiments, the set of compliance criteria 120 may be publicly available via electronic networks such as the Internet, or may be accessible via other media, subscriptions or channels.

Returning to FIG. 2, the documented care record 104 conforming to or based on the documented care template 122 may thus contain or require data, inputs or fields or other clinical measures 106 or metrics including laboratory test results required to support a given diagnosis or treatment, patient data including age, identification and medical history data, clinical data such as body temperature or blood pressure records, lung capacity test results, outpatient treatments, pharmaceutical prescriptions, physical therapy schedules or other clinical measures, laboratory results. The documented care record 104 may in embodiments be transmitted to and stored in a clinical data store 110 as a comprehensive longitudinal electronic medical record including a number of care records for a particular patient or as part of an aggregate record, for archiving, processing and further use.

According to embodiments of the invention in one regard, the documented care record 104 may likewise include, require or invoke clinical or diagnostic computations 108, which computations may include for example comparatively detailed information such as ratios on clinical measures or metrics such as the percentage of patient population which receives blood oxygen readings in a given period, the percentage of patients diagnosed with community acquired pneumonia (CAP) who receive specified prescribed antibiotics, or other ratios, metrics, variables or computations. According to embodiments in a further regard, the documented care record 104 may therefore automatically include an array of clinical information captured while the clinical care encounter is in process or approximately contemporaneously thereto, including to automatically generate, require or record clinical ratios and other diagnostic computations 108 required by Medicare, Medicaid or other compliance or other clinical authorities, without manual intervention.

In embodiments, the set of compliance criteria 120 and supporting documented care record 104 may likewise require that patient outcomes information such as morbidity, mortality, re-infection, total hospital time from admittance to discharge or other rates, statistics, data or other outcomes, at individual patient or collective levels, be generated and for example stored to clinical data store 110 in documented care record 104 or other structure or record. The documented care record 104 and any related information captured and stored to clinical data store 110 or otherwise may in turn be transmitted to regulatory body 112, for instance to CMS, JCAHO or other federal, state, local, private, industry or other body, agency or organization. According to embodiments of the invention in one regard, the transmission or delivery of the documented care record 104 to regulatory body may be performed on an automated basis, for instance by electronic transmission to regulatory body 112 upon completion of billing tasks, on a daily or an end of month basis, or on other scheduled, batch, event-triggered, ad hoc or other scheduling basis. That transmission may in other embodiments likewise be performed or scheduled manually, or on a combination of automated and manually-entered schedules.

Figure 3:
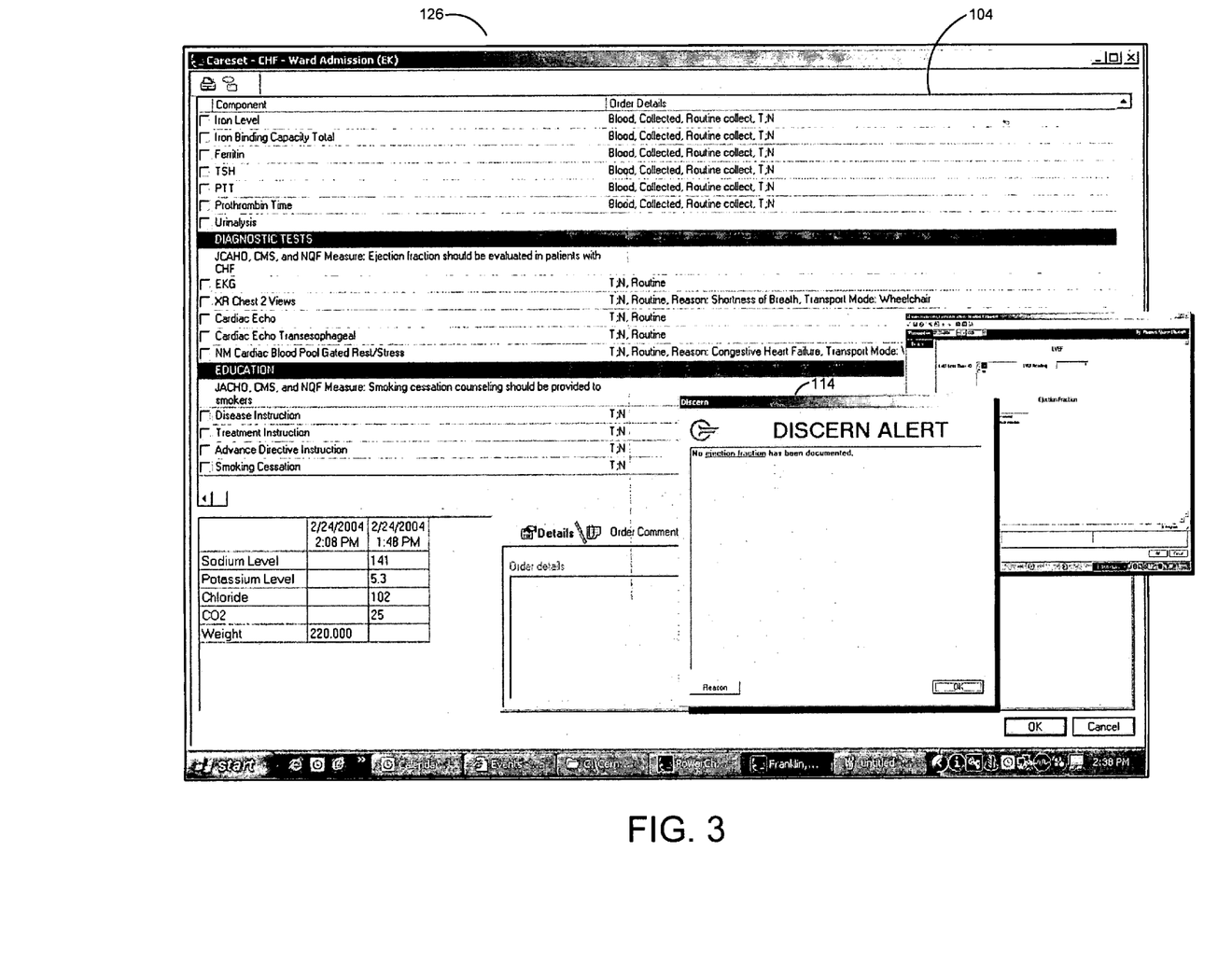
FIG. 3 illustrates a user interface for a compliance management user interface, according to embodiments of the invention.

According to embodiments of the invention in one regard, and as for example illustrated in FIG. 3, a compliance officer, care provider or other personnel may operate a user interface 126 to view, manipulate and store one or more documented care record 104, for instance via a computer workstation or other equipment or resource. According to embodiments of the invention in that regard, the user interface 126 may permit a compliance officer, care provider or other manager or personnel to examine, for instance, the documented care record 104 to view, identify, edit or confirm various clinical measures 106, diagnostic computations 108 and other clinically related information, including as illustrated documented blood tests or levels, symptom history and treatment or education (smoking cessation as illustrated) plan.

According to embodiments of the invention in a further regard, the user interface 126 may include or display one or more alert 114, indicating that a particular piece of compliance information is missing, incomplete, out of expected range or otherwise anomalous. Illustratively as shown, that alert 114 may indicate, for example, that no left ventricular ejection fraction has been documented or recorded for a given cardiac patient, which may for instance prompt a dialog to record reasons why that clinical measure has not been documented. According to embodiments of the invention in this regard, exceptions to necessary compliance data may therefore be automatically trapped and presented to the site's compliance officer or other personnel. In manual systems in contrast this type of data is rarely captured as users may often forget or neglect to document this information. Other types of indications or alerts based on other clinical data, fields or triggers are possible.

According to embodiments of the invention in a further regard, the user interface 126 may be, include or access an analytic tool or modeler to review, simulate and model compliance and clinical scenarios under different or changing conditions. For example, a compliance officer or other personnel may model the effects of improving clinical documentation for AMI patients on Medicare or Medicaid-funded reimbursements, or perform other comparisons, modeling or simulations. According to embodiments of the invention in one regard, analytic tools and resources such as those described in the aforementioned U.S. patent application Ser. No. 10/720,086 or other tools or platforms may be used for compliance and related modeling, including to model clinical outcomes and other projections.

Figure 4:
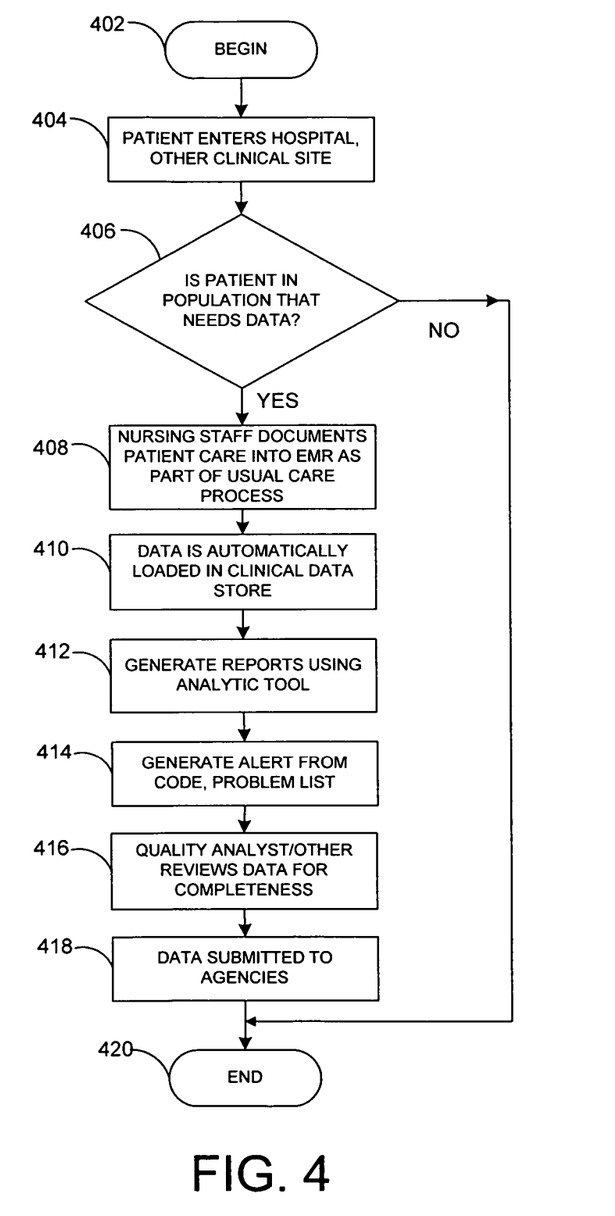
FIG. 4 illustrates a flowchart of overall compliance processing, according to embodiments of the invention.

Overall compliance data processing is illustrated in FIG. 4, according to embodiments of the invention in one regard. In step 402, processing may begin. In step 404, a patient or other care recipient may enter a hospital or other clinical facility, site or accommodation, including for instance an emergency room, clinically-equipped ambulance, helicopter or other transport or vehicle. In step 406, a determination may be made whether the patient lies within a population that requires capture of data for compliance purposes. If the determination is made in step 406 that compliance data for a particular patient or encounter is not required, processing may proceed to step 420 where processing may repeat, return to a prior processing point, jump to a further processing point or end. If the determination is made in step 406 that compliance data is mandated, processing may proceed to step 408 in which the nursing staff or other clinical personnel may document the patient's care into documented care record 104 or other component of an electronic medical record, as part of the routine provision of care to that patient. In step 410, at a schedule of every 24 hours or at other scheduled or unscheduled times, the documented care record 104 may be automatically transmitted or loaded into the clinical data store 110 or other data warehouse or facility.

In step 412, reports, charts, graphs or other analytic output may be generated based on the data stored to clinical data store 110 or otherwise, for instance using a compliance dashboard or tool including a user interface 126 or other resources to map, project and analyze the compliance, outcomes and other clinical or regulatory status of a patient, group of patients or other entity. In step 414, an alert 114 or other indicator or flag may be generated indicating that the documented care record 104 is missing information, contains incomplete or potentially inaccurate information, or has other anomalies or potential exceptions, for instance using a code, problem list or other triggers or data.

In step 416, a quality analyst or other human reviewer may review the documented care record 104 or other data for completeness, anomalies or other content. In step 418, the documented care record 104 and any associated or other data may be transmitted to a regulatory body 112, for instance via an electronic transmission, hard copy transmission or otherwise. In step 420, processing may repeat, return to a prior processing point, jump to a further processing point or end.

The foregoing description of the invention is illustrative, and modifications in configuration and implementation will occur to persons skilled in the art. For instance, while the invention has generally been described in terms of a point of care 102 located in a hospital, emergency room or related settings, in embodiments the point of care 102 may be or include other local, remote or mobile sites, for example including remote robotic operating rooms or remote diagnostic sites, ambulances, EMT or other vehicles, or other locations, sites, facilities or equipment.

Similarly, while the invention has in embodiments been described as generating a single documented care record 104 for a given patient or patient encounter, in embodiments more than one documented care record 104 may be generated, including for a single encounter or one procedure or event, which records for example may be stored and supplied to meet the compliance requirements of more than one regulatory body for the same or related clinical events. Further, while the invention has in embodiments been described as operating on a documented care record 104 which reflects clinical encounter information for a single patient, in embodiments the documented care record 104 may reflect or aggregate information related to multiple patients. Other hardware, software or other resources described as singular may in embodiments be distributed, and similarly in embodiments resources described as distributed may be combined. The scope of the invention is accordingly intended to be limited only by the following claims.

What is claimed is:

1. One or more computer readable storage media having computer executable instructions embodied thereon that, when executed by a computing device, perform a method for capturing compliance-qualified data, the method comprising:
   receiving a set of identifying information associated with a patient at a point of care;
   accessing patient information indicating membership of the patient in a group chosen from the set consisting of: an insurer, private payor, public payor, federal payor, Medicaid payor, and Medicare payor; and
   determining whether the patient lies within a population for which capture of compliance data is mandated by the patient's group, wherein:
      upon determining that the patient lies within a population for which capture of compliance data is not mandated by the patient's group:
         ending compliance processing automatically, thereby preventing creation of a list of one or more items that require attention to meet compliance reporting requirements;
         preventing the generation of an alert of the one or more items that require attention; and
         preventing a quality analysis of the alert of the one or more items that require attention; and wherein;
      upon determining that the patient lies within a population for which capture of compliance data is mandated by the patient's group:
         accessing a set of group-indicated compliance requirements relevant to the patient based on the indicated patient group and the required compliance data;
         generating a documented care template based on the set of group-indicated compliance requirements;
         capturing a set of compliance-qualified data based on the set of group-indicated compliance requirements included in the documented care template at the point of care;
         creating from a set of group-indicated compliance requirements a list of one or more items that require attention to meet compliance reporting requirements; and
         generating an alert of the one or more items that require attention consisting of one or more of: an indicator, a user-interface element, a flag, a dialog box, and a problem description, from said list.

2. The one or more computer readable storage media according to claim 1, further comprising a step of storing the set of compliance-qualified data to a clinical data store.

3. The one or more computer readable storage media according to claim 1, wherein receiving the set of identifying information associated with the patient or encounter at the point of care comprises receiving the set of identifying information associated with the patient or encounter at one or more of a hospital site, an urgent care site, a research site, a mobile care delivery vehicle and a pharmaceutical dispensing site.

4. The one or more computer readable storage media according to claim 1, further comprising a step of transmitting the set of compliance-qualified data to a compliance body.

5. The one or more computer readable storage media according to claim 4, wherein transmitting the set of compliance-qualified data to the compliance body comprises transmitting the set of compliance-qualified data to at least one of a government body and an industry body.

6. The one or more computer readable storage media according to claim 5, wherein transmitting the set of compliance-qualified data to the at least one of the government body and the industry body comprises transmitting the set of compliance-qualified data to a government body that determines at least clinical cost payment or reimbursement based on the set of compliance-qualified data.

7. The one or more computer readable storage media according to claim 5, wherein transmitting the set of compliance-qualified data to the at least one of the government body and the industry body comprises transmitting the set of compliance-qualified data to an industry body that determines at least an accreditation status based on the set of compliance-qualified data.

8. The one or more computer readable storage media according to claim 1, wherein generating a documented care template based on the set of compliance requirements comprises generating the documented care template based on a set of clinical measures.

9. The one or more computer readable storage media according to claim 8, wherein generating the documented care template based on the set of clinical measures comprises generating the documented care template based on at least one of blood-derived test ratios, patient population ratios and clinical outcome ratios.

10. The one or more computer readable storage media according to claim 1, wherein generating a documented care template based on the set of compliance requirements comprises generating an extensible documented care template.

11. The one or more computer readable storage media according to claim 1, further comprising a step of analyzing analytic scenarios based on the set of compliance-qualified data.

12. One or more computer readable storage media having computer executable instructions embodied thereon that, when executed by a computing device, perform a method for capturing a set of compliance-qualified data, the method comprising:
   receiving patient information indicating group membership of the patient in a group chosen from the set consisting of: an insurer, private payor, public payor, federal payor, Medicaid payor, and Medicare payor; and
   determining whether the patient lies within a population for which capture of compliance data is mandated by the patient's group, wherein:
      upon determining that the patient lies within a population for which capture of compliance data is not mandated by the patient's group:
         ending compliance processing automatically, thereby preventing creation of a list of one or more items that require attention to meet compliance reporting requirements;
         preventing the generation of an alert of the one or more items that require attention; and
         preventing a quality analysis of the alert of the one or more items that require attention; and wherein;
      upon determining that the patient lies within a population for which capture of compliance data is mandated by the patient's group:
         determining what compliance data is required for the patient at a point of care based on the information indicating group membership;
         generating a documented care template based on a set of group-indicated compliance requirements for the patient based on the information indicating group membership;

conditioning the capture of a set of compliance-qualified data on the set of group-indicated compliance requirements included in the documented care template at the point of care;

creating from a set of group-indicated compliance requirements a list of one or more items that require attention to meet compliance reporting requirements; and generating an alert of the one or more items that require attention consisting of one or more of: an indicator, a user-interface element, a flag, a dialog box, and a problem description, from said list.

13. The one or more computer readable storage media according to claim 12, wherein the method further comprises a step of storing the set of compliance-qualified data to a clinical data store.

14. The one or more computer readable storage media according to claim 12, wherein determining that compliance data is required for the patient or encounter at the point of care comprises determining that compliance data is required for the patient or encounter at least one or more of a hospital site, an urgent care site, a research site, a mobile care delivery vehicle and a pharmaceutical dispensing site.

15. The one or more computer readable storage media according to claim 12, wherein the method further comprises a step of transmitting the set of compliance-qualified data to a compliance body.

16. The one or more computer readable storage media according to claim 15, wherein transmitting the set of compliance-qualified data to the compliance body comprises transmitting the set of compliance-qualified data to at least one of a government body and an industry body.

17. The one or more computer readable storage media according to claim 16, wherein transmitting the set of compliance-qualified data to the at least one of a government body and an industry body comprises transmitting the set of compliance-qualified data to a government body that determines at least clinical cost payment or reimbursement based on the set of compliance-qualified data.

18. The one or more computer readable storage media according to claim 16, wherein transmitting the set of compliance-qualified data to the at least one of a government body and an industry body comprises transmitting the set of compliance-qualified data to an industry body that determines at least an accreditation status based on the set of compliance-qualified data.

19. The one or more computer readable storage media according to claim 12, wherein generating a documented care template based on the set of compliance requirements comprises generating a documented care template based on a set of clinical measures.

20. The one or more computer readable storage media according to claim 19, wherein generating a documented care template based on the set of clinical measures comprises generating a documented care template based on at least one of blood-derived test ratios, patient population ratios and clinical outcome ratios.

21. The one or more computer readable storage media according to claim 12, wherein generating the documented care template based on the set of compliance requirements comprises generating an extensible documented care template.

22. The one or more computer readable storage media according to claim 12, wherein the method further comprises a step of modeling analytic scenarios based on the set of compliance-qualified data.

23. One or more computer readable storage media having computer executable instructions embodied thereon that, when executed by a computing device, perform a method for capturing a set of compliance-qualified data, the method comprising:

accessing patient information indicating membership of a patient in a group;

determining on the basis of said patient information whether the patient lies within a population that requires capture of compliance data;

upon determining that said patient lies within a population that does require the capture of compliance data, performing compliance processing comprising:

accessing a set of group-indicated compliance requirements relevant to the patient based on the indicated patient group and the required compliance data;

generating a documented care template based on the set of group-indicated compliance requirements;

capturing a set of compliance-qualified data based on the set of group-indicated compliance requirements included in the documented care template at a point of care;

creating from a set of compliance requirements for the patient's group a list of one or more items that require attention to meet compliance reporting requirements, generating an alert of the one or more items that require attention consisting of one or more of: an indicator, a user-interface element, a flag, a dialog box, and a problem description, from said list, providing said alert to a quality analyst, and transmitting a compliance qualified report to a compliance agency based on the set of group-indicated compliance requirements; and upon determining that said patient lies within a population that does not require capture of compliance data:

ending compliance processing automatically, thereby preventing the creation of a list of one or more items that require attention to meet compliance reporting requirements, preventing the generation of an alert of the one or more items that require attention, and preventing a quality analysis of an alert of the one or more items that require attention.

24. The one or more computer readable storage media according to claim 23, further comprising a step of storing a set of compliance-qualified data to a clinical data store.

25. The one or more computer readable storage media according to claim 23, further comprising receiving a set of identifying information associated with the patient or encounter at a point of care.

26. The one or more computer readable storage media according to claim 25, wherein receiving the set of identifying information associated with the patient or encounter at the point of care comprises receiving a set of identifying information associated with the patient or encounter at one or more of a hospital site, an urgent care site, a research site, a mobile care delivery vehicle and a pharmaceutical dispensing site.

27. The one or more computer readable storage media according to claim 23, wherein transmitting the compliance-qualified report to the compliance agency comprises transmitting the set of compliance-qualified data to at least one of a government body and an industry body.

28. The one or more computer readable storage media according to claim 27, wherein transmitting the compliance-qualified report to the at least one of the government body and the industry body comprises transmitting the set of compliance-qualified data to a government body that determines at least clinical cost payment or reimbursement based on the set of compliance-qualified data.

29. The one or more computer readable storage media according to claim 27, wherein transmitting the compliance-qualified report to the at least one of the government body and the industry body comprises transmitting the set of compliance-qualified data to an industry body that determines at least an accreditation status based on the set of compliance-qualified data.

30. The one or more computer readable storage media according to claim 23, further comprising generating a documented care template based on a set of compliance requirements.

31. The one or more computer readable storage media according to claim 30, wherein the step of generating a documented care template based on the set of compliance requirements comprises generating the documented care template based on a set of clinical measures.

32. The one or more computer readable storage media according to claim 31, wherein generating the documented care template based on the set of clinical measures comprises generating the documented care template based on at least one of blood-derived test ratios, patient population ratios and clinical outcome ratios.

33. The one or more computer readable storage media according to claim 30, wherein generating a documented care template based on the set of compliance requirements comprises generating an extensible documented care template.

34. The one or more computer readable storage media according to claim 23, further comprising a step of analyzing analytic scenarios based on the set of compliance-qualified data.

* * * * *